United States Patent
Sekiguchi et al.

(10) Patent No.: US 8,982,342 B2
(45) Date of Patent: Mar. 17, 2015

(54) METHOD AND APPARATUS FOR CALCULATING A REFRACTIVE INDEX, MATERIAL FOR CALCULATING A REFRACTIVE INDEX, AND A TOMOGRAPHY APPARATUS

(71) Applicant: Canon Kabushiki Kaisha, Tokyo (JP)

(72) Inventors: Ryota Sekiguchi, Kawasaki (JP); Oichi Kubota, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/782,225

(22) Filed: Mar. 1, 2013

(65) Prior Publication Data
US 2013/0235367 A1    Sep. 12, 2013

(30) Foreign Application Priority Data

Mar. 11, 2012  (JP) .................................. 2012-053894
Feb. 18, 2013  (JP) .................................. 2013-028580

(51) Int. Cl.
| G01N 21/41 | (2006.01) |
| G01N 21/45 | (2006.01) |
| G01N 21/3586 | (2014.01) |
| G01N 21/3563 | (2014.01) |

(52) U.S. Cl.
CPC ................ *G01N 21/41* (2013.01); *G01N 21/45* (2013.01); *G01N 21/3586* (2013.01); *G01N 21/3563* (2013.01)
USPC .............................. 356/128; 356/130; 356/51

(58) Field of Classification Search
CPC .............. G01N 21/41; G01N 21/3586; G01N 21/4795; G01N 21/45; G01N 21/3563
USPC ................ 356/128–137, 630, 51; 250/338.1, 250/341.8, 330
See application file for complete search history.

(56) References Cited

U.S. PATENT DOCUMENTS

| 5,748,318 A * | 5/1998 | Maris et al. .................... 356/630 |
| 5,949,562 A | 9/1999 | Kubota et al. |
| 6,078,047 A | 6/2000 | Mittleman et al. |
| 6,661,519 B2 * | 12/2003 | Fukasawa ....................... 356/432 |
| 7,019,845 B1 * | 3/2006 | Leary et al. .................... 356/504 |
| 7,050,178 B2 * | 5/2006 | Morath et al. ................. 356/630 |
| 7,551,269 B2 * | 6/2009 | Itsuji ............................... 356/51 |
| 7,593,099 B2 * | 9/2009 | Ohtake et al. ............... 356/237.2 |
| 7,728,296 B2 * | 6/2010 | Cole et al. ................... 250/338.1 |

(Continued)

FOREIGN PATENT DOCUMENTS

| JP | 11-108845 | 4/1999 |
| JP | 2011-112548 | 6/2011 |

OTHER PUBLICATIONS

"Terahertz Sensing Technology," Section 4.2.2. Reflectance Spectroscopy, pp. 289-201.

*Primary Examiner* — Sang Nguyen
(74) *Attorney, Agent, or Firm* — Fitzpatrick, Cella, Harper & Scinto (57) ABSTRACT

A method of calculating, using a computer, a refractive index of at least a portion of a specimen by using electromagnetic wave measurement. The method includes measuring a first scattered waveform from a structure of the specimen, measuring a second scattered waveform from a structure, in which a material for calculating a refractive index is disposed on a surface of the specimen, and comparing intensities of peak positions at corresponding portions of the first scattered waveform and the second scattered waveform.

18 Claims, 7 Drawing Sheets

(56) References Cited

U.S. PATENT DOCUMENTS 7,787,122 B2* 8/2010 Saito et al. .................... 356/432
7,977,116 B2* 7/2011 Kasai et al. .................. 436/164
2001/0029436 A1* 10/2001 Fukasawa .................... 702/117
2008/0013071 A1* 1/2008 Tsumura et al. ................ 356/51
2010/0148069 A1* 6/2010 Ouchi ........................ 250/341.8
2012/0223229 A1* 9/2012 Itsuji ............................ 250/330

* cited by examiner

METHOD AND APPARATUS FOR CALCULATING A REFRACTIVE INDEX, MATERIAL FOR CALCULATING A REFRACTIVE INDEX, AND A TOMOGRAPHY APPARATUS

CLAIM OF PRIORITY

This application claims the benefit of Japanese Patent Applications No. 2012-053894, filed Mar. 11, 2012, and No. 2013-028580, filed Feb. 18, 2013, which are hereby incorporated by reference herein in their entirety.

BACKGROUND OF THE INVENTION

1. Field of the Invention

The present invention relates to (i) a calculation method and an apparatus for obtaining at least one of information regarding a refractive index and a thickness of a specimen by utilizing the fact that a propagation state of an irradiated electromagnetic wave changes due to the refractive index or a dielectric constant of the specimen, (ii) a material for calculating a refractive index, and (iii) a tomography apparatus.

2. Description of the Related Art

Calculation of the refractive index has been used widely in an optical band, and the calculation is also considered recently to be important for electromagnetic waves in a frequency band of a millimeter wave and a terahertz wave (30 GHz or higher and 30 THz or lower) (hereafter also referred to simply as a terahertz wave). This is because physical properties such as a refractive index and a dielectric constant of a specimen in this frequency band are different from those in the optical band, and that these characteristic properties can be used for identifying physical properties in a tomography apparatus, or the like. For instance, many biomolecules and pharmaceuticals have characteristic absorption spectra in this frequency band. As methods of calculating the refractive index in this frequency band, the following methods have been typically used.

As one of the methods, there is known a method of calculating the refractive index by irradiating a specimen with an electromagnetic wave in this frequency band, and comparing a waveform of a reflected wave thereof with the original waveform, for example, in a case without the specimen (see Japanese Patent Application Laid-Open No. H11-108845). According to this method, it is possible to map the refractive index in a depth direction of the specimen. Therefore, the method is one of important algorithms for forming a tomogram.

In addition, as a base of this algorithm, the original waveform to be compared with the waveform of the reflected wave is important. A waveform of an incident wave is used in the above-mentioned example, but various variations can be considered, depending on an optical system and the specimen. For instance, there is known a method in which a Fresnel reflection waveform on a surface of an attenuated total reflection (ATR) prism used in an optical system, called an attenuated total reflection spectroscopy, is used as the original waveform to be compared (see D. Woolard, W. Loerop, and M. Shur, translated by Omori and Hirose, "Terahertz Sensing Technology, vol. 1", NTS publication (2006) chapter eight, page 289). In the optical system of the ATR spectroscopy, in which the ATR prism and the specimen contact closely with each other, it is possible to eliminate an influence of a refractive index of the ATR prism. Therefore, it is possible to obtain the refractive index of the specimen at high sensitivity.

In the frequency band of the millimeter wave and the terahertz wave (30 GHz or higher and 30 THz or lower), absorption by water, however, cannot be neglected. Therefore, the algorithm of Japanese Patent Application Laid-Open No. H11-108845, in which an approximation of neglecting electromagnetic wave absorption is used, is difficult to be applied to a specimen, such as a biomolecule, having a relatively large electromagnetic wave absorption. This is because Fresnel loss and absorption loss cannot be distinguished between the waveform of the reflected wave and the original waveform to be compared. Therefore, depending on the specimen, it is difficult for the conventional method to calculate a refractive index distribution or a dielectric constant distribution in the depth direction of the specimen.

SUMMARY OF THE INVENTION

The present invention has been made in view of the above-mentioned problem, and it is an object thereof to provide a technology for enabling mapping of a refractive index or a dielectric constant in the depth direction even for a specimen, such as a biological material, having a relatively large electromagnetic wave absorption.

According to an exemplary embodiment, the present invention provides a method of calculating a refractive index of at least a portion of a specimen by using electromagnetic wave measurement, the method including measuring a first scattered waveform from a structure of the specimen, measuring a second scattered waveform from a structure in which a material for calculating a refractive index is disposed on a surface of the specimen, and comparing intensities at corresponding portions of the first scattered waveform and the second scattered waveform.

Further features of the present invention will become apparent from the following description of exemplary embodiments, with reference to the attached drawings.

DESCRIPTION OF THE EMBODIMENTS

In the present invention, as an original waveform to be compared with a scattered wave, there is used a waveform in a case when a minute change is applied to an electromagnetic wave structure inside a specimen (a structure that affects a propagation state of an irradiated electromagnetic wave). Therefore, when constituting an apparatus, the apparatus structure includes a material for calculating refractive index applied to or disposed an a surface layer of the specimen for performing tomography. The material for calculation is a material affecting the specimen so as to slightly change the refractive index inside the specimen. For instance, there is a material being used, such as Vaseline® or urea ointment containing water or oil, or a wetting material, such as a nano-capsule used for drug delivery of an endermic drug, which permeates into a living organism, or the like, from the surface layer. Without being limited to a liquid, a mist or a vapor may be used. If the specimen is a living organism, water vapor is constantly evaporating from the surface of the living organism due to the metabolism of the organism. Therefore, it is also possible to slightly change the refractive index inside the specimen by using a blocking material, such as glass or plastic, covering the specimen as the material for calculation. It is preferred to use quartz, polyethylene, Teflon®, polyolefin, or the like, having permeability for the THz wave.

Hereafter, with reference to the drawings, embodiments and examples of the present invention are described.

Embodiment 1

Figure 1:
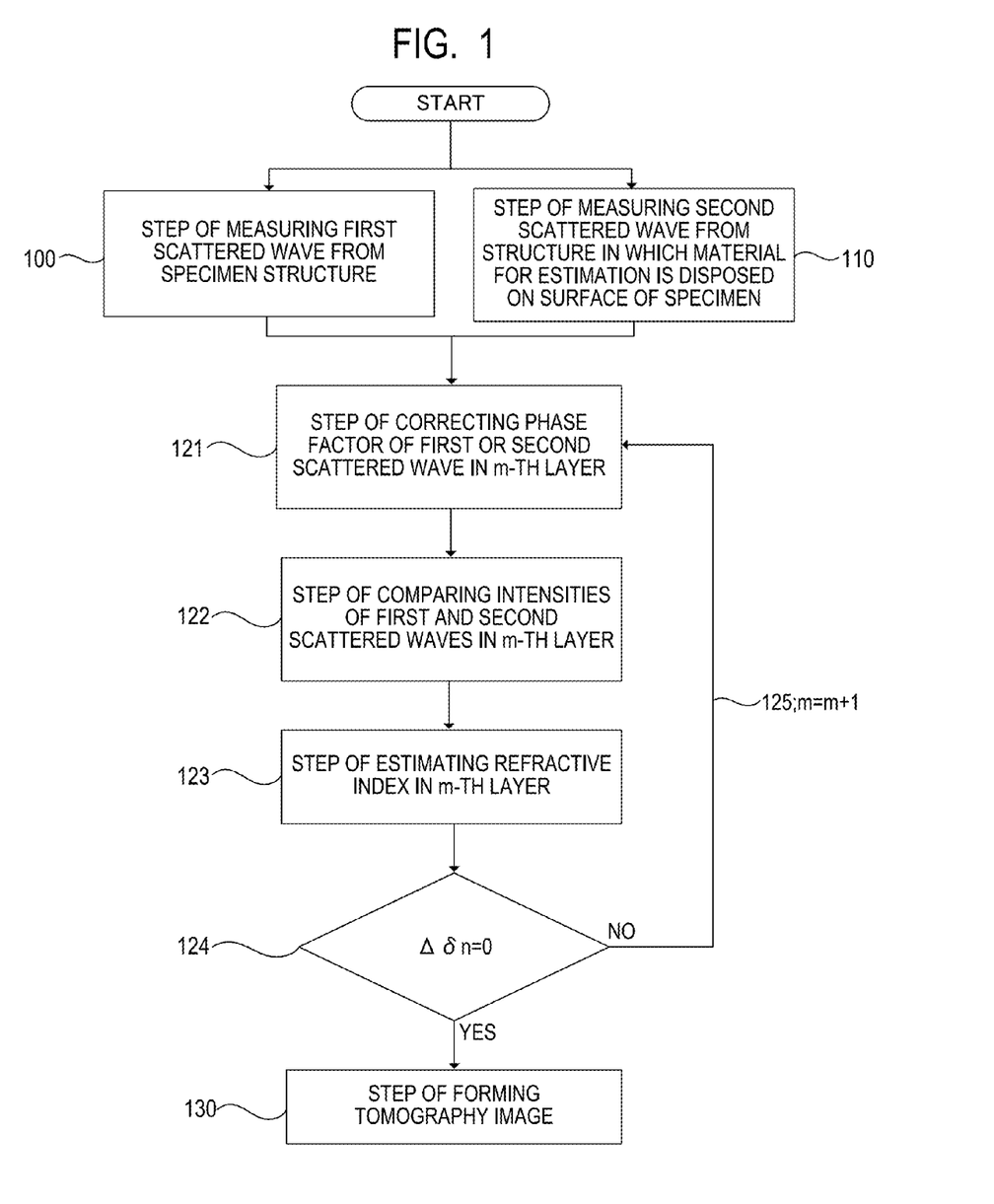
FIG. 1 is a diagram illustrating a flowchart of a refractive index calculation algorithm according to Embodiment 1.
Figure 2A:
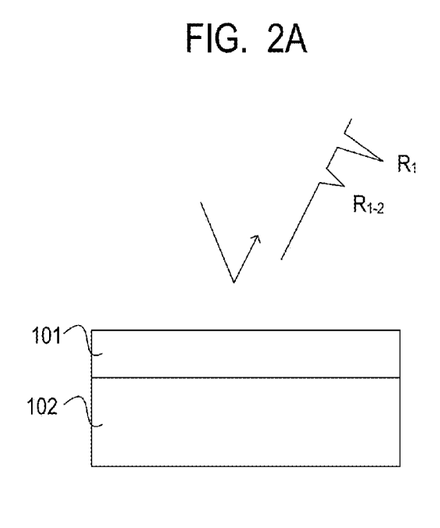
FIGS. 2A and 2B are diagrams illustrating a positional relationship between a specimen and a material for calculating refractive index according to Embodiment 1.
Figure 2B:
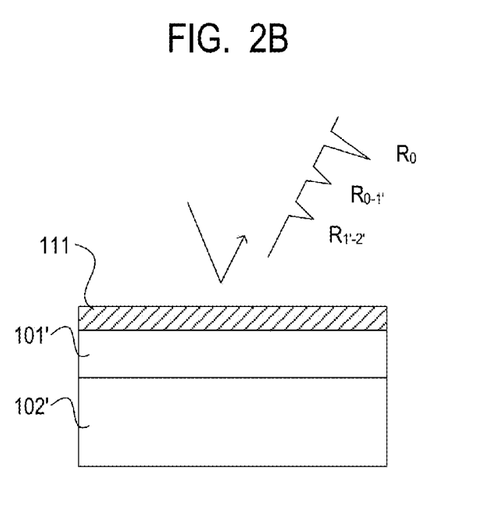

A refractive index calculation method using electromagnetic wave measurement and a material for calculating refractive index according to this embodiment are described with reference to FIGS. 1, 2A, and 2B. FIG. 1 is a flowchart of a refractive index calculation algorithm according to this embodiment. FIG. 2A is a diagram of a layout of a specimen when Step 100 is performed, and FIG. 2B is a diagram of a layout of the specimen and the material for calculation when Step 110 is performed. Note that, a first layer 101' and a second layer 102' of FIG. 2B are the same, respectively, as a first layer 101 and a second layer 102 of FIG. 2A. However, when a material for calculation 111 is a wetting material, for example, the welting material may permeate into the first layer 101 and the second layer 102. Therefore, the first layer is denoted by 101', and the second layer is denoted by 102' in FIG. 2B.

The algorithm of this embodiment includes Step 100 of measuring the scattered wave from the specimen structure, and Step 110 of measuring the scattered wave from the structure in which the material for calculating refractive index 111 is disposed on a surface of the specimen. The scattered wave includes a transmitted wave, a specular reflected wave and a diffuse reflected wave These steps may be performed in parallel or in series. If the wetting material as the material for calculation 111 dries slowly, it is preferred that Step 100 and Step 110 be performed in this order. FIG. 1 illustrates a case in which the steps are performed in parallel. In either case, this algorithm needs the two data. The scattered wave obtained in Step 100 is referred to as a first scattered wave, and the scattered wave obtained in Step 110 is referred to as a second scattered wave. Analysis of these data is performed as described below.

First the refractive index of the first layer 101 of the specimen is calculated. For this purpose, this algorithm includes Step 121 of correcting a phase factor (phase rotation) of the first or second scattered wave. Step 121 is performed for correcting a phase shift due to the material for calculation 111, and is performed easily by multiplying an amplitude of one of the scattered waves by $\text{Exp}(j \cdot n_{111} \cdot k_0 \cdot d_{111})$, because the thickness $d_{111}$ or the refractive index $n_{111}$ of the material for calculation 111 is known. Here, j is an imaginary unit, and $k_0$ is the wavenumber of the electromagnetic wave in a vacuum. In addition, if is possible to use one of the known thickness $d_{111}$ and refractive index $n_{111}$ so as to determine the other.

Next, the algorithm includes Step 122 of comparing intensities of the first and second scattered waves as to the first layer 101. The first and second scattered waves always have scattered waves of corresponding portions based on the same interface (for example, $R_1$ and $R_{0-1'}$), and thus an intensity ratio (for example, $R_1/R_{0-1'}$) is obtained by selecting the surface on an incident side of the first layer 101 of the specimen. This intensity ratio is approximately equal to a Fresnel loss ratio of the related interface as shown by Expression (1).

$$\frac{R_1}{R_{0-1'}} = \frac{\frac{(1-n_{101})^2 + \kappa_{101}^2}{(1+n_{101})^2 + \kappa_{101}^2}}{\frac{(n_{111}-n_{101})^2 + \kappa_{101}^2}{(n_{111}+n_{101})^2 + \kappa_{101}^2} \frac{16 n_{111}^2}{((1+n_{111})^2)^2}} \quad \text{(Ex. 1)}$$

$$\approx \frac{\frac{(1-n_{101})^2}{(1+n_{101})^2}}{\frac{(n_{111}-n_{101})^2}{(n_{111}+n_{101})^2} \frac{16 n_{111}^2}{((1+n_{111})^2)^2}}$$

In Step 123 of determining the refractive index $n_{101}$ of the first layer 101 of the specimen, this relationship is used to calculate the refractive index. Note that, an imaginary part $\kappa_{101}$ is temporarily neglected, provided that $n_{101} \gg \kappa_{101}$ holds. The intensity ratio is used here, but it is possible to use a time domain waveform, or the like, to obtain an amplitude ratio, and accurately select a true solution from multiple solutions in a case of the intensity ratio. When the scattered wave is the reflected wave, a phase inversion relationship may be used for calculating a solution. In addition, at this time point, the thickness $d_{101}$ of the first layer of the specimen can be easily determined based on a relationship between the determined $n_{101}$ and The measured optical distance (namely, an interval between a peak position of the first scattered wave $R_1$ and a peak position of the second scattered wave $R_{1-2}$). In other words, a thickness of the specimen at a portion for which the refractive index is calculated can be calculated based on the refractive index of the specimen calculated by the refractive index calculation method of this embodiment. Therefore, this embodiment may be regarded as a thickness calculation method When a minute change δn of the refractive index inside the specimen by the material for calculation 111 is not zero (No in determination 124), the process proceeds to a loop 125 of calculating a refractive index of the second layer 102 of the specimen (a loop proceeding to the (m+1)th layer of the specimen). The material for calculation 111 is a wetting material, for example, which permeates into at least the first layer 101, and a minute change of the refractive index is given. Thus, the process can proceed to at least the second layer 102. A refractive index of the second layer 102 of the Specimen is calculated. For this purpose, this algorithm includes Step 121 of correcting a phase factor of the first or second scattered wave. Step 121 is performed for determining a minute change δn of the refractive index by the material for calculation 111 (obtained by comparing an interval between the peak position of the first scattered wave $R_1$ and the peak position of the second scattered wave $R_{1-2}$ with an interval between a peak position of a second scattered wave $R_{0-1'}$ and a peak position of a third scattered wave $R_{1'-2'}$), and for correcting the minute change δn. Then, any one of the scattered wave amplitudes is multiplied by $\text{Exp}(j \cdot \delta n_{101} \cdot k_0 \cdot d_{101})$ as a trial, to determine the minute change δn so that a phase difference between the scattered waves (for example, $R_{1-2}$ and $R_{1'-2'}$) at the corresponding portions based on the same interface becomes zero.

Next, the algorithm includes Step 122 of comparing intensities of the first and second scattered waves as to the second layer 102. The first and second scattered waves always have scattered waves based on the same interface (for example, $R_{1-2}$ and $R_{1'-2'}$) and thus an intensity ratio (for example, $R_{1-2}/R_{1'-2'}$) is obtained by selecting the surface on an incident side of the second layer 102 of the specimen. This intensity ratio is approximately equal to a Fresnel loss ratio of the related interface as shown by Expression (2).

$$\frac{R_{1-2}}{R_{1'-2'}} = \frac{\frac{(n_{101}-n_{102})^2 + (\kappa_{101}-\kappa_{102})^2}{(n_{101}+n_{102})^2 + (\kappa_{101}+\kappa_{102})^2} \frac{16(n_{101}^2 + \kappa_{101}^2)}{((1+n_{101})^2 + \kappa_{101}^2)^2}}{\frac{(n_{101}+\delta n_{101}-n_{102})^2 + (\kappa_{101}-\kappa_{102})^2}{(n_{101}+\delta n_{101}+n_{102})^2 + (\kappa_{101}+\kappa_{102})^2} \frac{16 n_{111}^2}{((1+n_{111})^2)^2} \frac{16 n_{111}^2((n_{101}+\delta n_{101})^2 + \kappa_{101}^2)}{((1+n_{111})^2)^2((n_{111}+n_{101}+\delta n_{101})^2 + \kappa_{101}^2)^2}}$$

$$\approx \frac{\frac{(n_{101}-n_{102})^2}{(n_{101}+n_{102})^2} \frac{16 n_{101}^2}{((1+n_{101})^2)^2}}{\frac{(n_{101}-\delta n_{101}-n_{102})^2}{(n_{101}+\delta n_{101}+n_{102})^2} \frac{16 n_{111}^2}{((1+n_{111})^2)^2} \frac{16 n_{111}^2 (n_{101}+\delta n_{101})^2}{((n_{111}+n_{101}+\delta n_{101})^2)^2}}$$

(Ex. 2)

In Expression (2), attenuation $\mathrm{Exp}(-2\kappa_{101} \cdot k_0 \cdot d_{101})$ of the scattered wave amplitude due to absorption by the first layer 101 of the specimen is cancelled in the denominator and the numerator, respectively. Therefore, the Fresnel loss and the absorption loss are separated. In Step 123 of determining the refractive index $n_{102}$ of the second layer 102 of the specimen, this relationship is used to calculate the refractive index. Here, in the same manner, an imaginary part $\kappa_{102}$ is temporarily neglected, provided that $n_{102} \gg \kappa_{102}$ holds. Note that, at this time point, the imaginary part $\kappa_{101}$ in the first layer 101 of the specimen can be restored. For instance, an intensity ratio of the first scattered wave between the scattered waves based on the front surface (for example, $R_1$) and the back surface (for example, $R_{1-2}$) of the first layer 101 is a function of $n_{101}$, $n_{102}$, and $\kappa_{101}$. Because $n_{101}$ and $n_{102}$ are known at this time point, $\kappa_{101}$ can be determined. Therefore, the value $\kappa$ that was temporarily neglected can be restored as necessary at the time point when the refractive index of the next layer is calculated. In this embodiment, refractive indexes can be determined sequentially until the m-th layer of the specimen by repeating the process. When the minute change $\delta n$ of the refractive index of the m-th layer of the specimen is zero or small, the determination 124 is performed so as not to proceed to calculation of the refractive index of the (m+1)th layer 102 of the specimen. Finally, Step 130 is performed so as to form a tomogram by mapping the refractive indexes until the m-th layer of the specimen, and this algorithm is completed. Note that, it is preferred in this algorithm that an influence of the material for calculation 111 be larger on the front surface side of the specimen ($n_{111} > \delta n_{101} > \delta n_{102} > \delta n_{103}$ and so on). When the material for calculation 111 is a wetting material, for example, this assumption holds. This method can be performed, as illustrated in FIGS. 2A and 2B, by acquiring the first scattered wave as to the specimen structure (including the first layer 101 and the second layer 102), and further by acquiring the second scattered wave as to the structure in which the material for calculating refractive index 111 is disposed on the surface of the same specimen.

Embodiment 2

Figure 3:
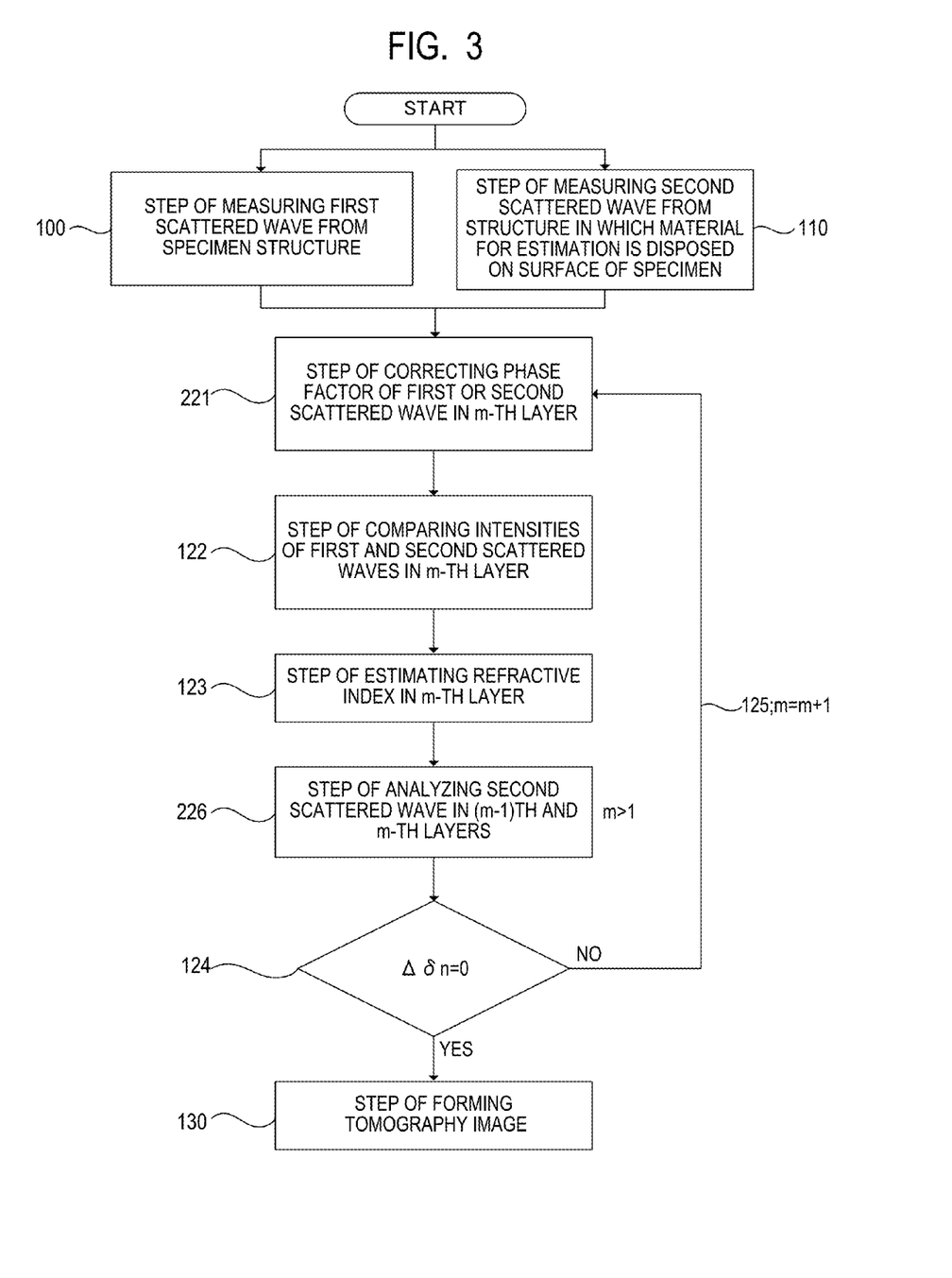
FIG. 3 is a diagram illustrating a flowchart of a refractive index calculation algorithm according to Embodiment 2.

A refractive index calculation method using electromagnetic wave measurement and a material for calculating refractive index according to Embodiment 2 are described with reference to FIG. 3. FIG. 3 is a flowchart of a refractive index calculation algorithm according to this embodiment. This embodiment shows a modification example of Embodiment 1. There are variations of the refractive index calculation algorithm, and, for instance, the algorithm as illustrated in FIG. 3 may be adopted. In addition to the method of Embodiment 1 in which the minute change $\delta n$ of the refractive index inside the specimen by the material for calculation 111 is mainly considered, a minute change $\delta d$ of the thickness of the layer inside the specimen is also considered in this embodiment. This embodiment is different from Embodiment 1 in Steps 221 and 226.

In Step 221 of correcting a phase factor of the first or second scattered wave, the minute change $\delta d$ of the thickness of the layer by the material for calculation 111 is also determined, and any minute change $\delta d$ is corrected. For this purpose, either one of the scattered wave amplitudes is multiplied by $\mathrm{Exp}(j \cdot \delta n_{101} \cdot k_0 \cdot (d_{101}+\delta d_{101}))$ as a trial, and a set of $\delta n$ and $\delta d$ is determined so that a phase difference between the scattered waves based on the same interlace (for example, $R_{1-2}$ and $R_{1'-2'}$) becomes zero. However, in this step, only the set of $\delta n$ and $\delta d$ can be determined. Therefore, a temporary value $\delta n$ (determined in the manner as described in Embodiment 1) is used to perform Steps 122 and 123. After that, the algorithm includes Step 226 of analyzing the scattered wave as for the (m-1)th layer of the specimen. Step 226 is performed for determining $\delta n$ by another method. In this case, the Fresnel loss of the second scattered wave at the surface of the first layer 101' (for example, $R_{0-1'}$) is expressed by following Expression (3). This relationship is used to calculate $\delta n$.

$$R_{0-1'} = \frac{(n_{111}-n_{101}-\delta n_{101})^2 + \kappa_{101}^2}{(n_{111}+n_{101}+\delta n_{101})^2 + \kappa_{101}^2} \frac{16 n_{111}^2((n_{101}+\delta n_{101})^2 + \kappa_{101}^2)}{((n_{111}+n_{101}+\delta n_{101})^2 + \kappa_{101}^2)^2}$$

(Ex. 3)

In this Step 226, it is preferred to determine $\delta n_{101}$ in a recursive manner without neglecting $\kappa_{101}$ so that cancellation of significant digits does not occur. The method of determining $\kappa_{101}$ is performed as described above. When the material lor calculation 111 is a material such as water having a dielectric property similar to that of a biological material. $\delta n$ becomes relatively small, and hence, it is considered that $\delta d$ cannot be neglected. This embodiment is effective in this case.

Embodiment 3

Figure 4A:
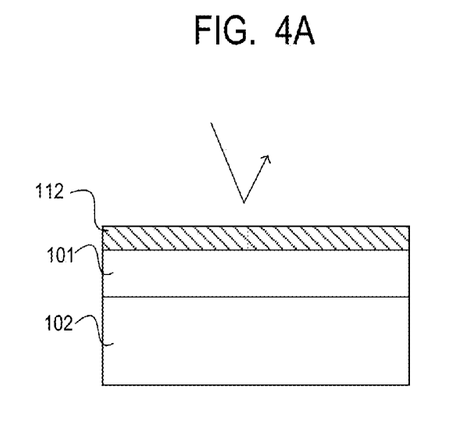
FIGS. 4A and 4B are diagrams illustrating a structure of a specimen and a material for calculating refractive index according to Embodiment 3.
Figure 4B:
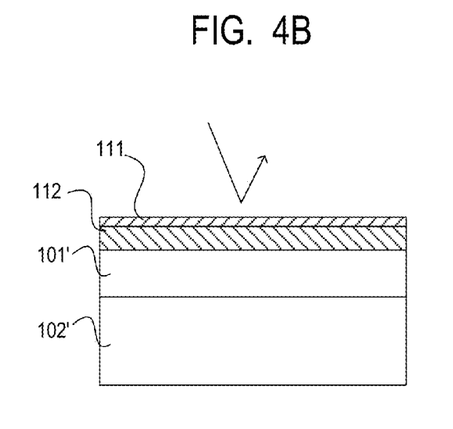
Figure 5A:
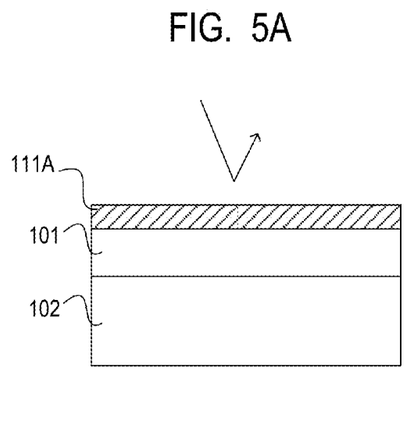
FIGS. 5A and 5B are diagrams illustrating a structure of a specimen and a material for calculating refractive index according to Embodiment 3.
Figure 5B:
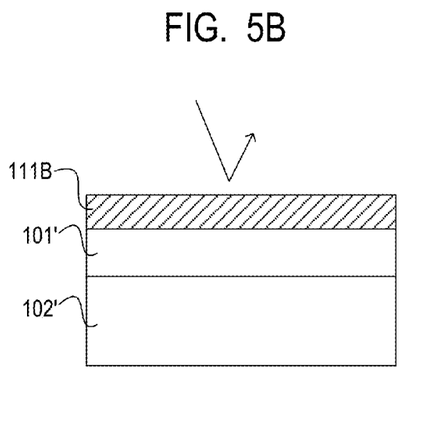

A refractive index calculation method using electromagnetic wave measurement and a material for calculating refractive index according to Embodiment 3 are described with reference to FIGS. 4A and 4B, and FIGS. 5A and 5B. FIG. 4A is a diagram of a layout of the specimen when Step 100 is performed, and FIG. 4B is a diagram of a layout of the specimen and the material for calculation when Step 110 is performed. In addition, FIG. 5A is a diagram of layout of the specimen when Step 100 is performed, and FIG. 5B is a diagram of a layout of the specimen and the material tor calculation when Step 110 is performed. Note that, the first layer 101' and the second layer 102' of FIGS. 4B and 5B are the same, respectively, as the first layer 101 and the second layer 102 of FIGS. 4A and 5A. However, when the material for calculation 111 is a wetting material, for example, the wetting material may permeate into the first layer 101 and the second layer 102. Therefore, the first layer is denoted by 101', and the second layer is denoted by 102' in FIGS. 4B and 5B.

This embodiment shows a modification example of Embodiment 1. There are variations of the layout of the specimen and the material for calculating refractive index. For instance, as illustrated in FIGS. 4A and 4B, in a case when the material for calculation 111 is disposed on the surface of the specimen structure including the first layer 101 and the second layer 102 via a certain layer 112, the algorithm of Embodiment 1 can be used as it is, by considering the specimen and the unknown layer 112 as an unknown specimen extended to include the unknown layer 112. in a case of the wetting material 111, the layer 112 may have an effect of promoting permeating. When materials for calculation 111A and 111B having different thicknesses are disposed on the surfaces of the specimen structures including the first layer 101 or 101' as illustrated in FIGS. 5A and 5B, it is possible to use one of the structures as the structure for the original waveform to be compared. When the material for calculation is a wetting material, it is considered that there occurs a difference of permeating depth due to the thickness. Therefore, by considering the specimen and the material for calculation (wetting material) 111A as an unknown specimen extended to include the material for calculation (wetting material) 111A in FIG. 5A, the algorithm of Embodiment 1 can be used as it is. However, for this purpose, it is a precondition that a difference of the thickness $\delta d_{111}$ or the refractive index $n_{111}$ of the material for calculation 111A is known.

A more specific refractive index calculation method, a material for calculating refractive index, and a tomography apparatus are described in the following examples.

Example 1

Figure 6A:
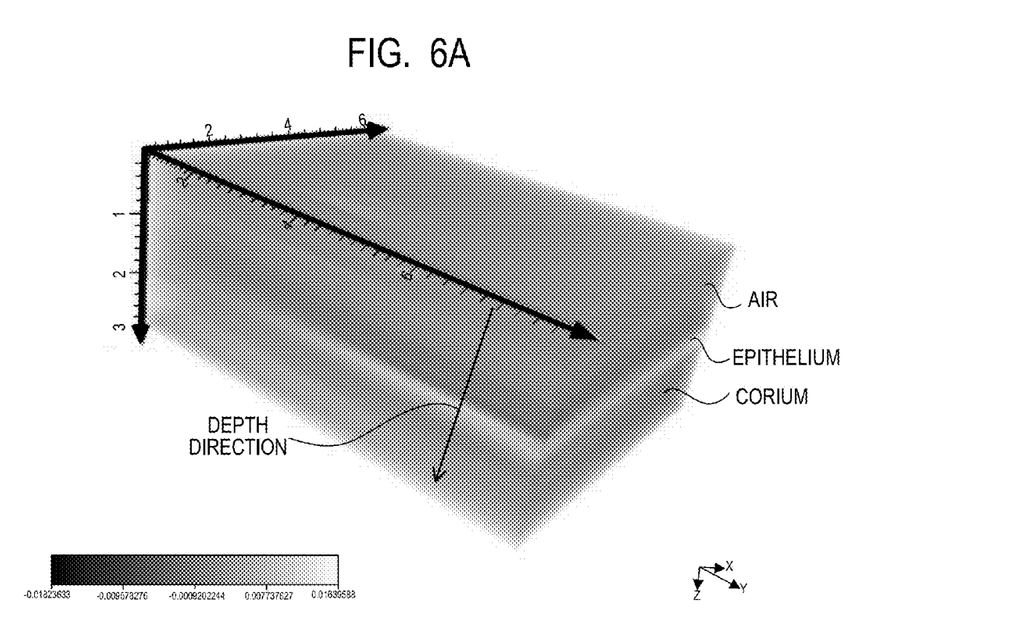
FIGS. 6A and 6B are diagrams illustrating a refractive index calculation method according to Example 1.
Figure 6B:
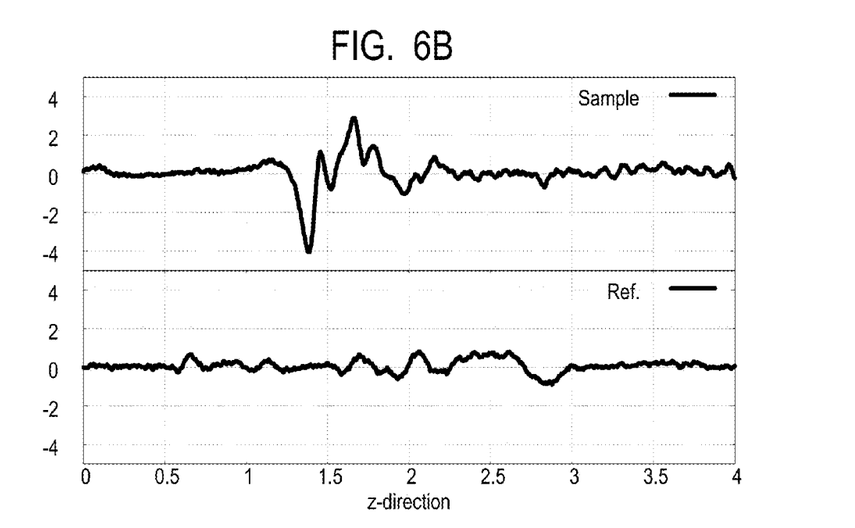

The refractive index calculation method and the material for calculating refractive index according to Example 1 are described with reference to FIGS. 6A and 6B. FIG. 6A is a tomogram of the specimen according to this example. FIG. 6B shows time-base waveforms of the reflected waves from the specimen and from the material for calculating refractive index according to this example.

In this example, a piece of pig skin is used as the specimen. A pig skin includes an epithelium (including keratin) 101 and a corium 102, and is similar to human skin. In addition, a terahertz time domain spectroscopic system (THz-TDS) is used for measuring a waveform of the scattered wave. As the terahertz wave, an electromagnetic wave pulse is used, which has a frequency of 0.5 THz at a highest intensity and a frequency band of approximately 4 THz. As the optical system, a general reflection system is used, so that the reflected wave from the specimen can he acquired. In this example, cream containing Vaseline® is used as the material for calculation 111. The material for calculation 111 may be applied to only a portion of the specimen. Thus, the above-mentioned first scattered wave and second scattered wave can be obtained.

FIG. 6A shows a tomogram of the pig skin acquired by the THz-TDS. In the image, the horizontal direction (x, y) represents a direction along the skin, and the vertical direction (z) represents a depth direction. This tomogram roughly includes three layers corresponding to the air, the epithelium, and the corium, arranged in order, from the top. In this example, at the point of x-y address (0, 6) in FIG. 6A, data of the reflected wave from the skin itself is acquired. In addition, in an area near the point of x-y address (2, 4), data of the reflected wave from the skin on which Vaseline® is applied to have a thickness of 0.35 mm is acquired. FIG. 6B shows time-base waveforms thereof, which are denoted by Sample and Ref., respectively. The individual waveforms have their peaks, which indicate information of the individual interface. Further, the information of the individual interlace is as shown in Table 1.

TABLE 1

Data of interfaces of specimen acquired by terahertz time domain spectroscopic system

| | Depth (Sample) | Amplitude (Sample) | Depth (Ref.) | Amplitude (Ref.) |
|---|---|---|---|---|
| Vaseline surface | | | 0.657 | 0.671 |
| Epithelium surface | 1.382 | −4.057 | 1.696 | 0.661 |
| Corium surface | 1.661 | 2.893 | 2.062 | 0.809 |

*Depth is optical distance in mm.

For instance, Sample has a peak of amplitude −4.057 at point 1.382 in the depth direction. Because Sample includes the epithelium surface and the corium surface (an interface between the corium and the epithelium), there are ideally two peaks. Because Ref. includes the Vaseline® surface and the epithelium surface (an interface between the epithelium and the Vaseline®), and the corium surface (an interface between the corium and the epithelium), there are ideally three peaks. In FIG. 6B, other unnecessary peaks are observed, but it is possible to determine whether they are ghosts or not based on horizontal continuity in the tomogram, or the like. In this example, peak detection is simply used. The above-mentioned algorithm of the present invention is applied to the data prepared in this way.

First, a phase factor shift due to the Vaseline® is corrected so as to calculate $n_{vaseline}$. In this example, the following Expression is used:

$$(1.696 - 0.657) = 2 \times n_{vaseline} \times 0.35.$$

Thus, $n_{vaseline} = 1.44$ is determined. In the right side, "2" indicates a path count of an outward path and an inward path. Next, in order to determine nepithelium, an amplitude ratio of the epithelium surfaces of Sample and Ref. is compared with the square root of the right side of above Expression (1). As a result, $n_{epithelium} = 1.37$ is easily calculated. Because sign information is contained in a case of the amplitude ratio, the calculation is easier than in the case of the intensity ratio. In other words, it is possible to select a solution of the calculated refractive index based on the signs of the amplitudes at the corresponding portions of the two scattered waves. Thus, $d_{epithelium} = 0.10$ mm can also be determined.

Next, correction of the phase factor shift due to moisture of the Vaseline® in the epithelium is performed to calculate $\delta n_{epithelium}$. In this example, the following Expression is used:

$$(2.062-1.696)-(1.661-1.382)=2\times\delta n_{epithelium}\times 0.10 \text{ mm}.$$

Thus, $\delta n_{epithelium}$ is 0.43. Otherwise, the following Expression is used to obtain the same result:

$$(1.661-1.382)/(2.062-1.696)=n_{epithelium}+\delta n_{epithelium}).$$

Next, in order to obtain $n_{corium}$, an amplitude ratio of the corium surfaces of Sample and Ref. is compared with the square root of the right side of the above Expression (2). As a result, $n_{corium}=1.99$ is easily calculated. As a result of applying this algorithm, the calculated information is as shown in Table 2. As described above first, not only the refractive index of the epithelium 101, but also, the refractive index of the corium 102 can be calculated. When there is a layer under the corium 102, the items indicated unknown can be calculated as a matter of course.

TABLE 2

Calculated data of interfaces of specimen

| | Thickness (Sample) | Refractive index (Sample) | Thickness (Ref.) | Refractive index (Ref.) |
|---|---|---|---|---|
| Vaseline | — | — | Known | 1.44 |
| Epithelium | 0.10 | 1.37 | 0.10 | 1.79 |
| Corium | Unknown | 1.99 | Unknown | Unknown |

*Depth is optical distance in mm.

The time-base waveform is used as an example in this example, but this is not a limitation. For instance, a waveform of an interferogram, or the like, may be used. Therefore, the system is not limited to the THz-TDS. When the interferogram is used, it is necessary to compare the intensity ratio instead of the amplitude ratio of the scattered wave. There are considered various methods of calculating the multiple solutions. For instance, there are considered a method involving selection using a database, or the like, and a method of giving auxiliary information such as thickness by another apparatus using an ultrasonic wave or light. As a matter of course, a known algorithm may be used at the same time.

In addition, the optical system may be a transparent system or a reflection system with a tilt angle. In this case, it is only needed to rewrite Expressions (1) and (2) appropriately by using Fresnel equations. Details thereof are omitted, but a case of the transparent system is as follows, for example. The first scattered wave is assumed to be the scattered wave containing a pulse after passing through the first layer 101 and the second layer 102 of the specimen, or a pulse after being reflected by the interface between the first layer 101 and the second layer 102, and by the interface between the air and the first layer 101 so as to pass through the first layer 101, and the second layer 102. In addition, the second scattered wave is assumed to be the scattered wave containing a pulse after passing through the material for calculation 111 and the first layer 101 and the second layer 102 of the specimen, a pulse after being reflected by the interface between the material for calculation 111, and the first layer 101 and by the interface between the air and the material for calculation 111 so as to pass through the material for calculation 111, the first layer 101, and the second layer 102, or a pulse after being reflected by the interlace between the first layer 101 and the second layer 102, and by the interface between the material for calculation 111 and the first layer 101, so as to pass through the first layer 101 and the second layer 102. As to the pulses after passing through multiple surfaces, including the same interface regarding the first and second scattered waves, an appropriate interface is selected so as to acquire the intensity ratio. Then, using the above-mentioned appropriately rewritten Fresnel equations, a measurement optical distance between pulses, and the like, the above-mentioned process is performed. In this manner, it is possible to calculate the refractive index, and the like, of the specimen layer by utilizing the transmitted light.

Example 2

Figure 7:
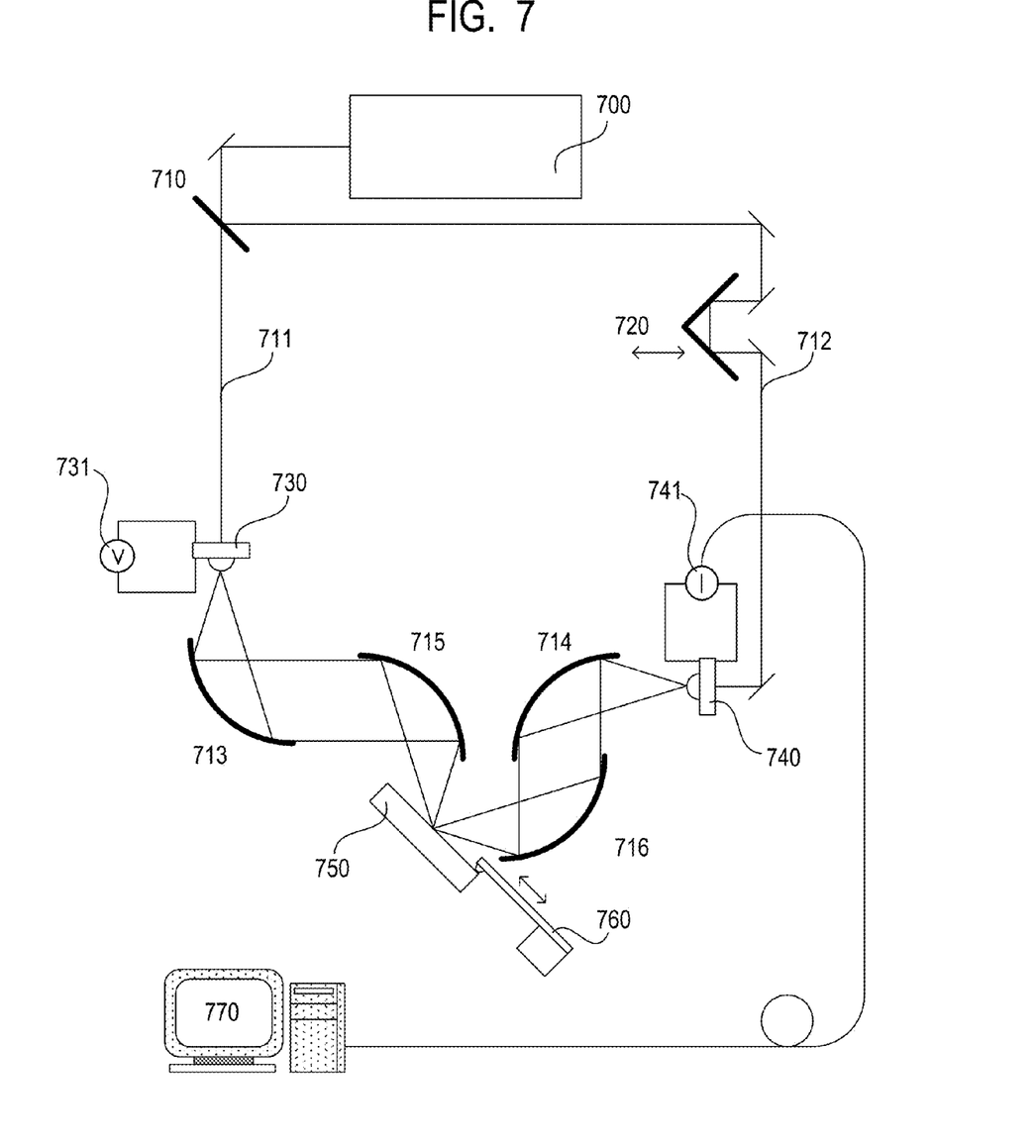
FIG. 7 is a diagram illustrating a structure of a tomography apparatus according to Example 2.

FIG. 7 illustrates an example of a tomographic imaging apparatus with a refractive index calculation apparatus and a terahertz time domain spectroscopic system (THz-TDS), which are constituted by using the refractive index calculation method and the material for calculating refractive index described above.

Such a spectroscopic system itself is basically the same as a conventional one. This spectroscopic system includes a short pulse laser 700, a half mirror 710, an optical delay system (delay unit) 720, an electromagnetic wave generation element (electromagnetic wave generation unit) 730, and an electromagnetic wave detection element (electromagnetic wave detection unit) 740 as main elements. A pump beam 711 and a probe beam 712 irradiate the electromagnetic wave generation element 730 and the electromagnetic wave detection element 740, respectively. A terahertz wave generated from the electromagnetic wave generation element 730, to which a voltage is applied from a voltage source 731, is guided by terahertz guides 713 and 715 to a specimen 750. The terahertz wave containing internal information of the specimen 750 is guided by terahertz guides 714 and 716 and is detected by the electromagnetic wave detection element 740. In this case, a current value detected by an ammeter 741 is proportional to the amplitude of the terahertz wave. In order to perform time resolution (namely, to acquire a time-base waveform of the electromagnetic wave), it is only needed to control irradiation timings of the pump beam and the probe beam by, for example, moving the optical delay system 720 tor changing an optical path length of the probe beam 712. In other words, the delay time between generation of the electromagnetic wave by the electromagnetic wave generation element 730 and detection of the electromagnetic wave by the electromagnetic wave detection element 740 is adjusted. This is a scan in the depth direction in the tomography.

Using the apparatus according to the Example 2, if there is a discontinuous portion of material inside the specimen, a reflected echo pulse appears at a time position corresponding to the discontinuous part in the signal to be acquired. A tomogram can be acquired by scanning the specimen 750 in a one-dimensional manner, and a three-dimensional image, as illustrated in FIG. 6A, can be acquired by scanning the specimen 750 in a two-dimensional manner. By connecting to an analysis system (signal processing unit) 770 such as a PC that can perform signal processing as described in Example 1, it is possible to map the refractive indexes inside the specimen. Further, the apparatus may include an application apparatus 760 as an application unit that can apply the material for calculating refractive index on the specimen with good control. As described above, the apparatus illustrated in FIG. 7 includes the electromagnetic wave generation unit for generating the electromagnetic wave for irradiating the specimen, the electromagnetic wave detection unit for detecting the electromagnetic wave from the specimen, the delay unit for adjusting the delay time between the generation of the electromagnetic wave by the electromagnetic wave generation unit and the detection of the electromagnetic wave by the electromagnetic wave detection unit, and the refractive index calculation apparatus including the signal processing unit for processing the signal from the electromagnetic wave detection unit. Then, the signal processing unit performs processes including the process of calculating the refractive index of at least a portion of the specimen by comparing intensities at the corresponding portions of the first and second scattered waves measured by the electromagnetic wave detection unit.

In this way, it is possible to constitute the tomographic imaging apparatus, the refractive index calculation apparatus, or the like, by using the refractive index calculation method, the material for calculating refractive index, and the like, according to the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and function.

What is claimed is:

1. A method of calculating, using a computer, a refractive index of at least a portion of a specimen by using electromagnetic wave measurement, the method comprising:
    measuring a first scattered waveform from a structure of the specimen;
    measuring a second scattered waveform from a structure, in which a material for calculating a refractive index is disposed on a surface of the specimen; and
    comparing intensities of peak positions at corresponding portions of the first scattered waveform and the second scattered waveform,
    wherein the step of comparing intensities of peak positions includes obtaining a ratio between the intensities at corresponding portions of the first scattered waveform and the second scattered waveform.

2. The method according to claim 1, wherein the material for calculation has a thickness and a refractive index, one of which is known.

3. The method according to claim 1, wherein the material for calculation comprises a material that affects the specimen so as to change the refractive index of at least a portion thereof.

4. The method according to claim 1, further comprising correcting phase rotations of the first scattered waveform and the second scattered waveform.

5. The method according to claim 1,
    wherein the step of comparing intensities includes comparing the ratio with an intensity ratio of Fresnel loss at an interface that relates to the corresponding portions.

6. The method according to claim 1, further comprising selecting a solution of the calculated refractive index based on a sign of the amplitudes at the corresponding portions of the scattered waveform.

7. The method according to claim 1, wherein the first scattered waveform and the second scattered waveform comprise a reflected wave.

8. A method of calculating a thickness of the specimen at a portion for which the refractive index is calculated, based on the refractive index of the specimen calculated by the method according to claim 1.

9. A material for calculating a refractive index to be used in the method of calculating a refractive index calculation according to claim 1, wherein the material is disposed on a surface of the specimen so as to change the refractive index of at least a portion thereof.

10. The material according to claim 9, wherein the material permeates the specimen so as to change the refractive index of at least a portion thereof.

11. The material according to claim 9, wherein the material blocks a substance generated from the specimen so as to change the refractive index of at least a portion thereof.

12. The method according to claim 1, wherein the first scattered waveform and the second scattered waveform are time-base waveforms, respectively.

13. An apparatus for calculating a refractive index of at least a portion of a specimen by using electromagnetic wave measurement, the apparatus comprising:
    an electromagnetic waveform generation unit for generating an electromagnetic waveform for irradiating the specimen;
    an electromagnetic waveform detection unit for detecting the electromagnetic waveform from the specimen;
    a delay unit for adjusting a delay time between generation of the electromagnetic waveform by the electromagnetic wave generation unit and detection of the electromagnetic waveform by the electromagnetic wave detection unit; and
    a signal processing unit for processing a signal from the electromagnetic waveform detection unit, wherein the signal processing unit calculates the refractive index of at least a portion of the specimen by comparing an intensity of a peak position of a first scattered waveform from a structure of the specimen and an intensity of a peak position of a second scattered waveform from a structure in which a material for calculating a refractive index is disposed on a surface of the specimen at corresponding portions, which are measured by the electromagnetic waveform detection unit,
    wherein comparing intensities of the peak positions by the signal processing unit includes obtaining a ratio between the intensities at corresponding portions of the first scattered waveform and the second scattered waveform.

14. The apparatus according to claim 13, further comprising an application unit for applying the material for calculating the refractive index on the specimen.

15. A method of calculating, using a computer, a refractive index of at least a portion of a specimen by using electromagnetic wave measurement, the method comprising:
    measuring a first scattered waveform from a structure of the specimen;
    measuring a second scattered waveform from a structure, in which a material for calculating a refractive index is disposed on a surface of the specimen; and
    comparing amplitudes of peak positions at corresponding portions of the first scattered waveform and the second scattered waveform,
    wherein the step of comparing amplitudes of peak positions includes obtaining a ratio between the amplitudes at corresponding portions of the first scattered waveform and the second scattered waveform.

16. The method according to claim 15,
    wherein the step of comparing amplitudes includes comparing the ratio with an amplitude ratio of Fresnel loss at an interface that relates to the corresponding portions.

17. A material for calculating a refractive index to be used in the method of calculating a refractive index calculation according to claim 15, wherein the material is disposed on a surface of the specimen so as to change the refractive index of at least a portion thereof.

18. An apparatus for calculating a refractive index of at least a portion of a specimen by using electromagnetic wave measurement, the apparatus comprising:

an electromagnetic waveform generation unit for generating an electromagnetic waveform for irradiating the specimen;
an electromagnetic waveform detection unit for detecting the electromagnetic waveform from the specimen;
a delay unit for adjusting a delay time between generation of the electromagnetic waveform by the electromagnetic wave generation unit and detection of the electromagnetic waveform by the electromagnetic wave detection unit; and
a signal processing unit for processing a signal from the electromagnetic waveform detection unit, wherein the signal processing unit calculates the refractive index of at least a portion of the specimen by comparing an amplitude of a peak position of a first scattered waveform from a structure of the specimen and an amplitude of a peak position of a second scattered waveform from a structure in which a material for calculating a refractive index is disposed on a surface of the specimen at corresponding portions, which are measured by the electromagnetic waveform detection unit,
wherein comparing amplitudes of the peak positions by the signal processing unit includes obtaining a ratio between the amplitudes at corresponding portions of the first scattered waveform and the second scattered waveform.

* * * * *